US008721705B2

(12) United States Patent
White et al.

(10) Patent No.: US 8,721,705 B2
(45) Date of Patent: May 13, 2014

(54) NON-FORESHORTENING INTRALUMINAL PROSTHESIS

(75) Inventors: Geoffrey Hamilton White, Sydney (AU); Russell J. Redmond, Goleta, CA (US); Alan K. Plyley, Goleta, CA (US)

(73) Assignee: Endosystems LLC CA (US)

( * ) Notice: Subject to any disclaimer, the term of this patent is extended or adjusted under 35 U.S.C. 154(b) by 1665 days.

(21) Appl. No.: 11/107,088

(22) Filed: Apr. 14, 2005

(65) Prior Publication Data

US 2005/0187610 A1    Aug. 25, 2005

Related U.S. Application Data

(60) Continuation of application No. 10/051,433, filed on Jan. 18, 2002, now Pat. No. 6,881,222, which is a division of application No. 09/416,994, filed on Oct. 13, 1999, now abandoned.

(51) Int. Cl.
*A61F 2/82* (2013.01)
*A61F 2/06* (2013.01)

(52) U.S. Cl.
USPC ........................................ 623/1.15

(58) Field of Classification Search
CPC ............... A61F 2/82; A61F 2/88; A61F 2/89; A61F 2/90; A61F 2/0063; A61F 2/04; A61F 2/06; A61F 2/91; A61F 2002/9155; A61F 2002/91558; A61B 17/11; A61B 2017/1132; E04G 1/06
USPC ...................... 623/1.15, 1.17, 1.16
See application file for complete search history.

(56) References Cited

U.S. PATENT DOCUMENTS

| 5,356,423 | A | | 10/1994 | Tibon et al. |
| 5,540,712 | A | | 7/1996 | Kleshinski et al. |
| 5,643,312 | A | | 7/1997 | Fischell et al. |
| 5,695,516 | A | * | 12/1997 | Fischell et al. ............... 606/194 |
| 5,716,393 | A | | 2/1998 | Lindenberg et al. |
| 5,733,303 | A | | 3/1998 | Israel et al. |
| 5,807,404 | A | | 9/1998 | Richter |
| 5,810,872 | A | | 9/1998 | Kanesaka et al. |
| 5,824,059 | A | | 10/1998 | Wijay |
| 5,855,600 | A | | 1/1999 | Alt |
| 5,902,317 | A | | 5/1999 | Kleshinski et al. |
| 5,922,021 | A | | 7/1999 | Jang |
| 5,938,697 | A | | 8/1999 | Killion et al. |
| 5,980,553 | A | | 11/1999 | Gray et al. |
| 6,022,371 | A | | 2/2000 | Killion |
| 6,053,941 | A | | 4/2000 | Lindenberg et al. |
| 6,056,776 | A | | 5/2000 | Lau et al. |
| 6,059,822 | A | * | 5/2000 | Kanesaka et al. ............ 623/1.15 |
| 6,066,167 | A | | 5/2000 | Lau et al. |
| 6,132,460 | A | | 10/2000 | Thompson |
| 6,206,911 | B1 | | 3/2001 | Milo |
| 6,299,635 | B1 | | 10/2001 | Frantzen |
| 6,312,460 | B2 | | 11/2001 | Drasler et al. |
| 6,348,065 | B1 | | 2/2002 | Brown et al. |
| 6,398,806 | B1 | | 6/2002 | You |
| 6,423,084 | B1 | | 7/2002 | St. Germain |
| 6,443,982 | B1 | | 9/2002 | Israel et al. |
| 6,730,116 | B1 | * | 5/2004 | Wolinsky et al. ............ 623/1.15 |
| 6,881,222 | B2 | * | 4/2005 | White et al. ................. 623/1.15 |

* cited by examiner

Primary Examiner — Brian E. Pellegrino
(74) Attorney, Agent, or Firm — Raymond Sun

(57) ABSTRACT

A stent has a plurality of cells disposed about the circumference of the stent, with at least one cell having a plurality of struts that are connected together to form the cell. At least one strut has a portion that compensates for foreshortening of the struts during expansion of the stent.

3 Claims, 17 Drawing Sheets

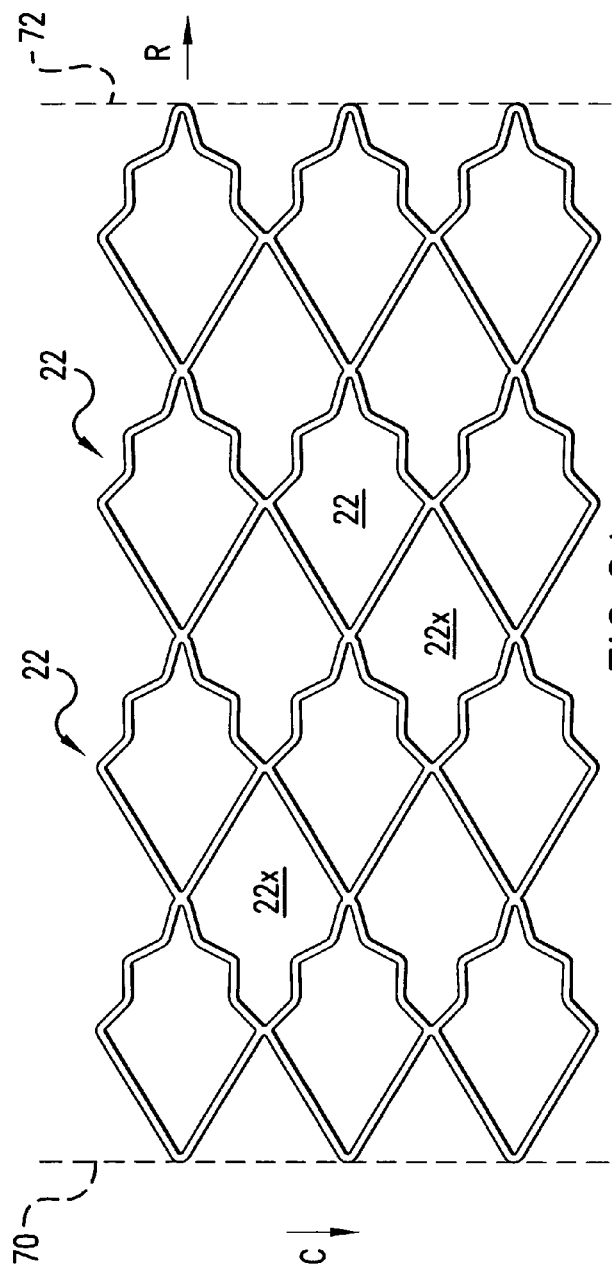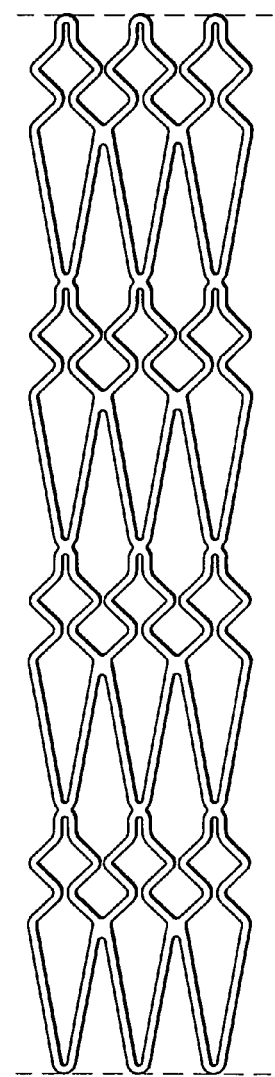
FIG.2A
FIG.2B

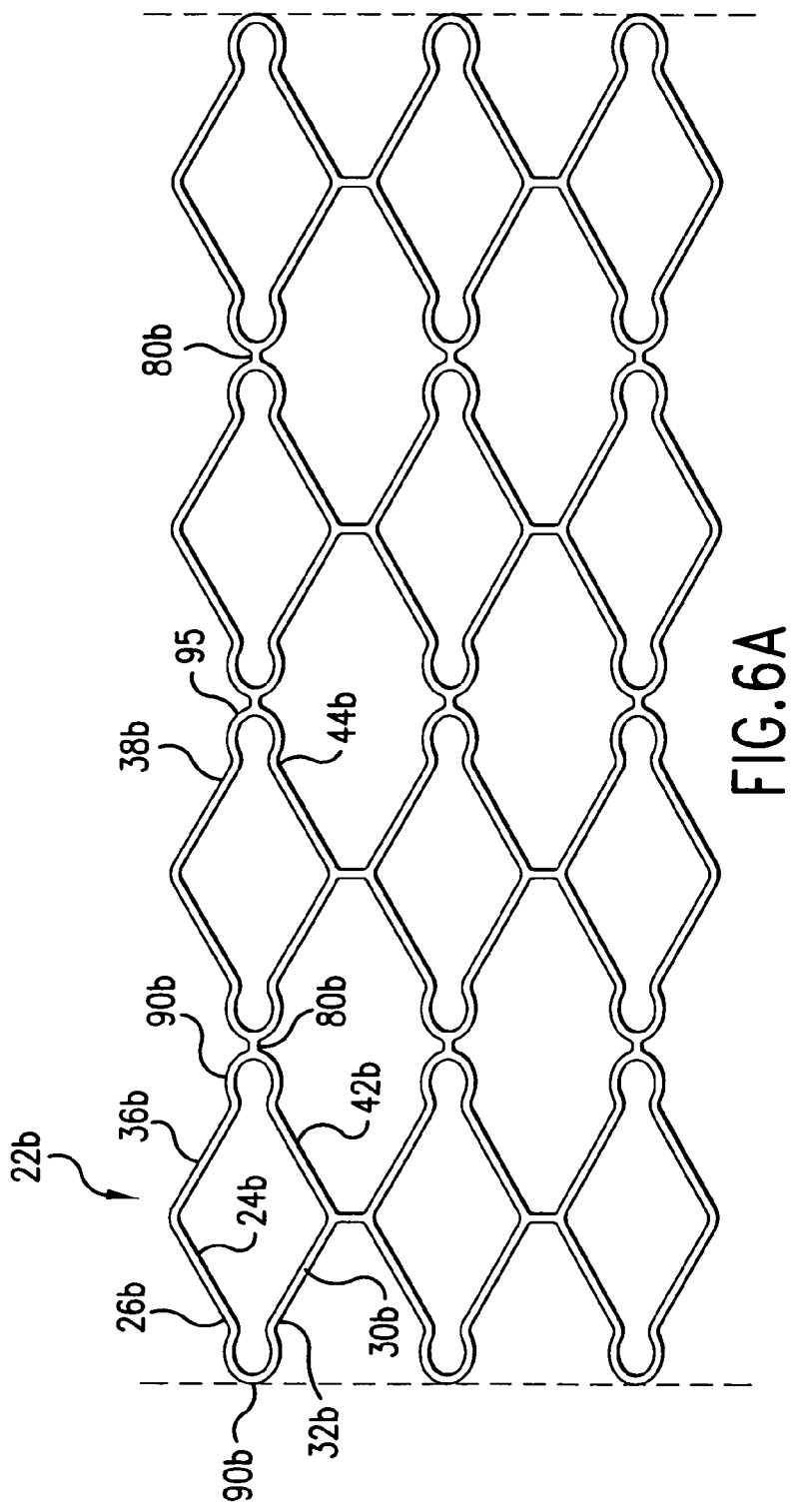
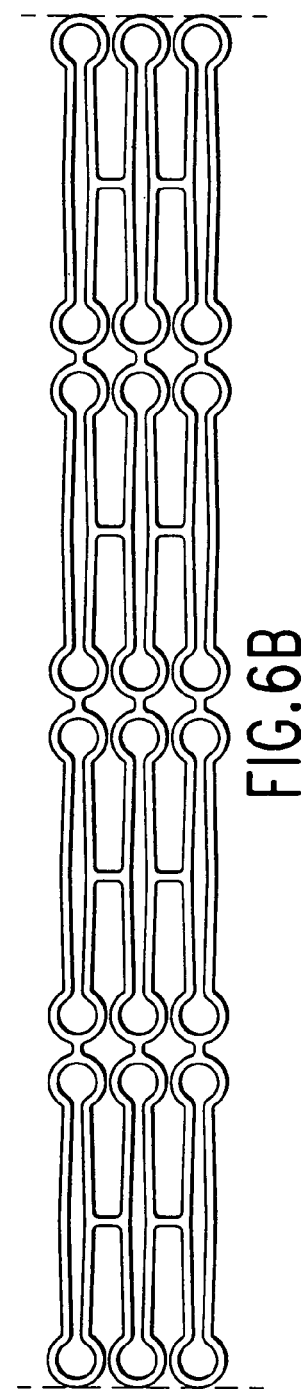
FIG.6A
FIG.6B

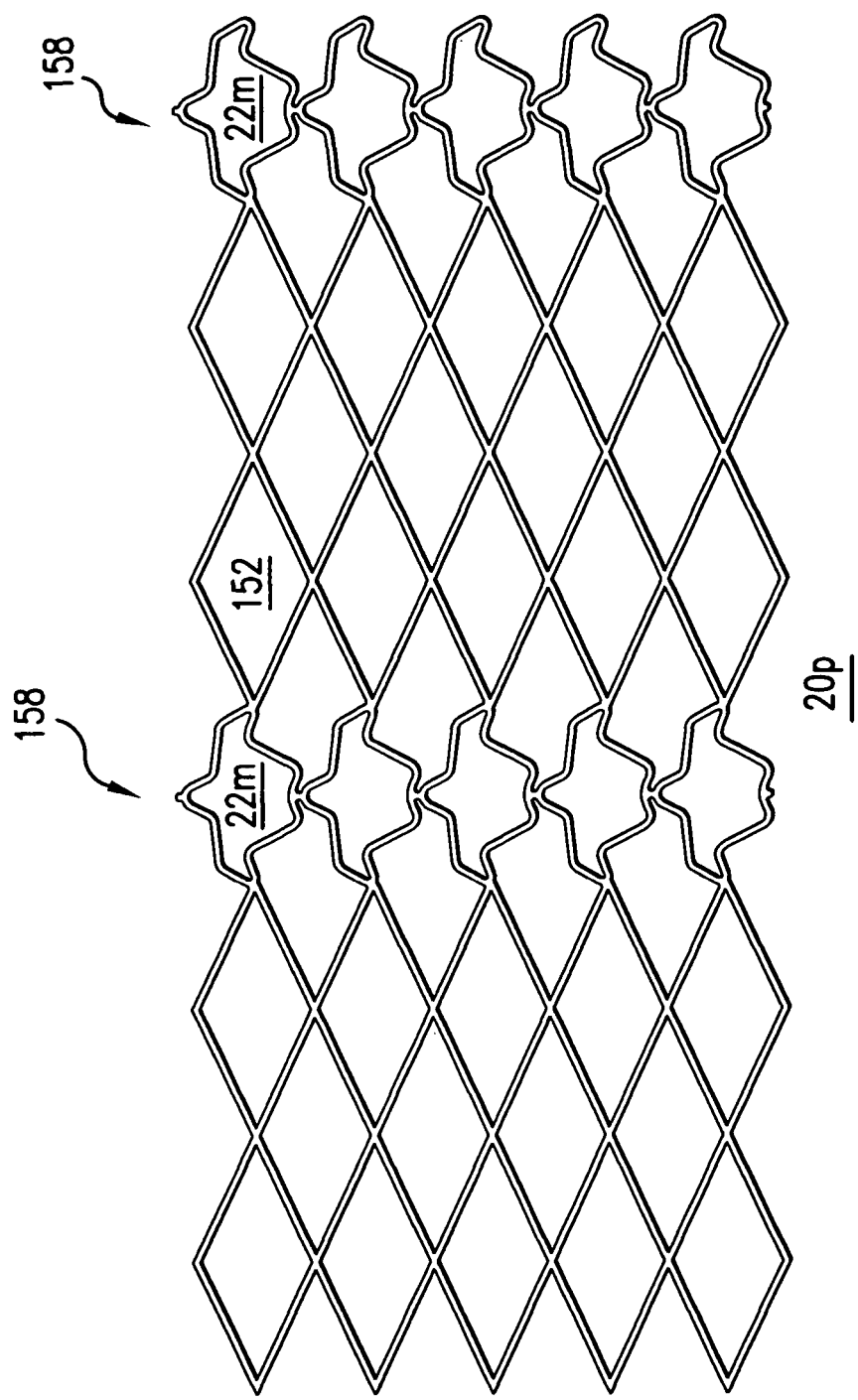

NON-FORESHORTENING INTRALUMINAL PROSTHESIS

This is a continuation of application Ser. No. 10/051,433, filed Jan. 18, 2002, now U.S. Pat. No. 6,881,222, which is in turn a division of Ser. No. 09/416,994, filed on Oct. 13, 1999, now abandoned.

BACKGROUND OF THE INVENTION

1. Field of the Invention

The present invention relates to intraluminal prostheses for implantation into a mammalian vessel, and in particular, to intraluminal stents that do not experience foreshortening in the longitudinal direction when the stent is deployed to an expanded state.

2. Description of the Prior Art

Intraluminal prosthesis, such as stents, are commonly used in the repair of aneurysms, as liners for vessels, or to provide mechanical support to prevent the collapse of stenosed or occluded vessels. These stents are typically delivered in a compressed state to a specific location inside the lumen of a vessel or other tubular structures, and then deployed at that location of the lumen to an expanded state. These stents have a diameter in their expanded state which is several times larger than the diameter of the stents in the compressed state. These stents are also frequently deployed in the treatment of atherosclerotic stenosis in blood vessels, especially after percutaneous transluminal coronary angioplasty (PTCA) procedures, to improve the results of the procedure and to reduce the likelihood of restenosis.

U.S. Pat. No. 5,733,303 (Israel et al.) and U.S. Pat. No. 5,827,321 (Roubin et al.) describe the problems associated with the foreshortening of intraluminal stents when such stents are expanded. In addition, U.S. Pat. No. 5,733,303 (Israel et al.) describes stents that have struts whose longitudinal length decreases when the stent expands, thereby causing the overall longitudinal length of the stent to foreshorten. These struts are connected by flexible connecting members, each having an area of inflection that functions to compensate for the foreshortening experienced by the struts during expansion of the stent.

Unfortunately, there are certain drawbacks associated with providing flexible connecting members that have areas of inflection. First, to accommodate the areas of inflection, these connecting members often create segments within the stent where the aperture or opening defined by these connecting members have a large size. Such increased aperture size may allow increased ingrowth of tissue (also known as "in-stent restenosis"). Second, curved areas of inflection on these connecting members may cause distortion of the lumen of the stent when the stent is twisted or experiences angulation in the longitudinal direction. Third, the connecting members form an area of weakness in the stent structure which may encourage kink of the stent at the site with flexion or angulation, or which in extreme circumstances may lead to stent breakage after experiencing repetitive stress. In other words, the provision of the connecting members decreases the amount of support that the stent can enjoy.

Thus, there still remains a need for an intraluminal prosthesis that maintains a consistent length in both its fully compressed and fully expanded states, while avoiding the disadvantages set forth above. There also remains a need for a stent which can accommodate body vessels having varying lumen diameters, different anatomies, and different disease states.

SUMMARY OF THE DISCLOSURE

It is an object of the present invention to provide an intraluminal prosthesis that maintains a consistent length in both its fully compressed and fully expanded states.

It is another object of the present invention to provide an intraluminal prosthesis that provides increased support throughout the prosthesis while minimizing the potential for stent kink or breakage at certain regions along the stent.

It is yet another object of the present invention to provide an intraluminal prosthesis that minimizes the potential for in-stent restenosis.

In order to accomplish the objects of the present invention, there is provided a stent having a plurality of cells disposed about the circumference of the stent, with at least one cell having a plurality of struts that are connected together to form the cell. At least one strut has a portion that compensates for foreshortening of the struts during expansion of the stent.

In another embodiment, the present invention provides a stent having a plurality of cells disposed about the circumference of the stent, with at least one cell having a plurality of double-struts that are connected together to form the cell.

Thus, the stent according to the present invention maintains a consistent length in both its fully compressed and fully expanded states, and in all states between its fully compressed and fully expanded states. As a result, the stent according to the present invention facilitates accurate sizing and deployment, thereby simplifying, and possibly reducing the time needed for, the medical procedure.

BRIEF DESCRIPTION OF THE DRAWINGS

FIG. 2A is a side elevational view of a portion of the stent of FIG. 1 in its expanded state;

FIG. 2B is a side elevational view of the portion of FIG. 2A in its compressed state;

FIG. 6A is a side elevational view of a portion of a stent according to another embodiment of the present invention;

FIG. 6B is a side elevational view of the portion of FIG. 6A in its compressed state;

FIGS. 16-18 illustrate modifications to the cell pattern of the stent of FIG. 15.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The intraluminal prosthesis according to the present invention is a stent, although the principles of the present invention are also applicable to other prosthesis such as liners and filters. The stent is delivered to a desired location in the lumen of a body vessel in a compressed state, and is then deployed by expanding it to its expanded state. The stent maintains substantially the same length in both its fully compressed and fully expanded states.

The stent according to the present invention can be a self-expanding stent, or a stent that is radially expandable by inflating a balloon or expanded by an expansion member, or a stent that is expanded by the use of radio frequency which provides heat to cause the stent to change its size. The stent may also be coated with coverings of PTFE, dacron, or other biocompatible materials to form a combined stent-graft or endovascular prosthesis. The vessels in which the stent of the present invention can be deployed include but are not limited to natural body vessels such as ducts, arteries, trachea, veins, ureters and the esophagus, and artificial vessels such as grafts.

Figure 1:
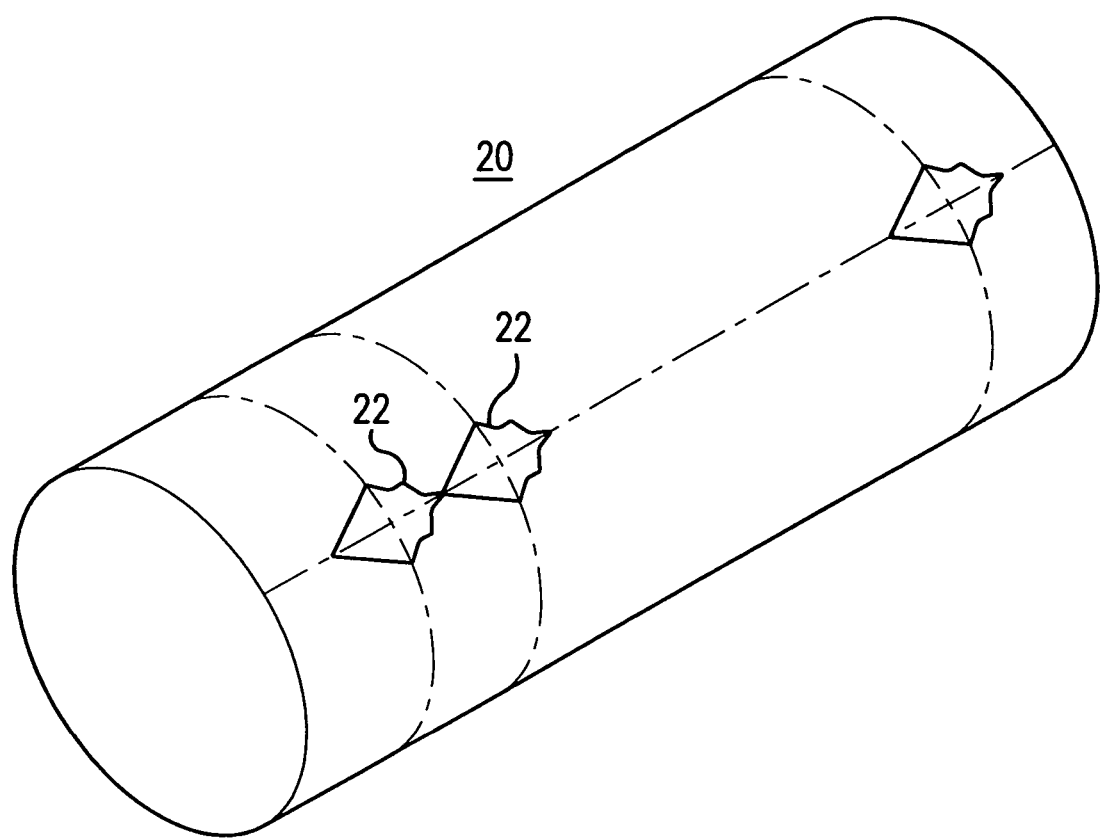
FIG. 1 is a perspective view of a stent according to one embodiment of the present invention.
Figure 3A:
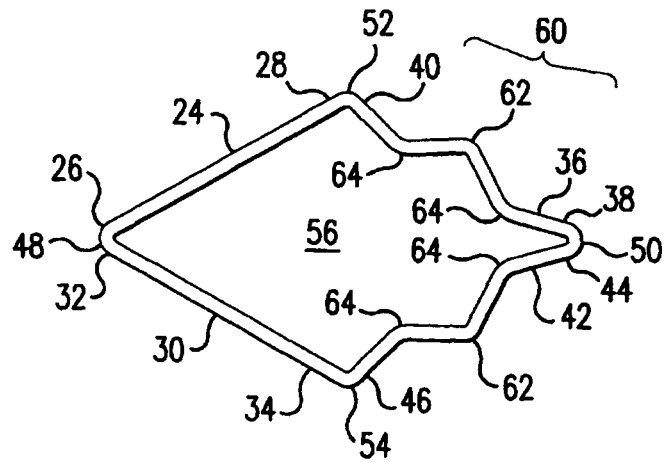
FIG. 3A is an enlarged side elevational view of a cell of the portion of FIG. 2A.

A stent 20 according to the present invention is illustrated in FIGS. 1, 2A and 3A in its expanded state. Referring to FIG. 1, the stent 20 has a tubular configuration and is made up of a plurality of cells that are comprised of generally V-shaped struts connected at their apices. FIGS. 2A and 2B illustrate a portion of the stent 20 in greater detail, and FIG. 3A illustrates one cell 22. Each cell 22 has a first strut 24 having a first end 26 and a second end 28, a second strut 30 having a first end 32 and a second end 34, a third strut 36 having a first end 38 and a second end 40, and a fourth strut 42 having a first end 44 and a second end 46. The first ends 26 and 32 of the first and second struts 24 and 30, respectively, are connected at a first apex 48, and the first ends 38 and 44 of the third and fourth struts 36 and 42, respectively, are connected at a second apex 50. The second ends 28 and 40 of the first and third struts 24 and 36, respectively, are connected to form a third apex 52, and the second ends 34 and 46 of the second and fourth struts 30 and 42, respectively, are connected to form a fourth apex 54, so that the four struts 24, 30, 36 and 42 together form an aperture or open space 56.

As shown in FIG. 2A, the first apex 48 of each cell 22 is connected to the second apex 50 of a longitudinally adjacent cell 22, and the third apex 52 of each cell 22 is connected to the fourth apex 54 of a transversely adjacent cell 22. For purposes of the present invention, cells 22 can be provided in longitudinal rows and transverse columns. Therefore, the first and second apices 48 and 50 of adjacent cells 22 are connected to form a row R of cells 22, while the third and fourth apices 52 and 54 of adjacent cells 22 are connected to form a column C of cells 22.

The struts 24, 30, 36 and 42 would normally experience foreshortening when the stent 20 is expanded. Therefore, any of the struts 24, 30, 36 and 42 can be provided with a compensating portion 60 that functions to compensate for the foreshortening experienced by the struts 24, 30, 36 and 42 during expansion of the stent 20. As shown in greater detail in FIG. 3A, each compensating portion 60 has at least one point of inflection. In the non-limiting example shown in FIG. 3A, the compensating portion 60 has three points of inflection 62 and 64 that are inflected in directions opposite to each other. One point of inflection 62 can be considered to be an external point of inflection since it extends outside the confines of the cell 22 as defined by the struts 24, 30, 36 and 42. Similarly, each of the other two points of inflection 64 can be considered to be an internal point of inflection since it extends into the aperture 56. Each compensating portion 60 can be provided along any portion of the strut 36 and 42, and slopes downwardly from one end of the strut 36 and 42 to an internal point of inflection 64, at which point it slopes upwardly to the external point of inflection 62, then slopes downwardly to the other internal point of inflection 64, before sloping upwardly again towards the other end of the strut 36 or 42. Thus, each compensating portion 60 has a plurality of alternating segments that are defined by the points of inflection 62 and 64.

As best shown in FIG. 2A, the pattern of cells 22 can define a second pattern of cells 22x that have about the same configuration as the cells 22, but reversed about a vertical axis defined by apices 52 and 54 to form a substantial mirror image of the cells 22. Each of the second cells 22x is defined by a separate strut from four separate cells 22. Like the cells 22, these second cells 22x are also arranged to form rows and columns of cells 22x.

As shown in FIG. 3A, each cell 22 has exactly ten points of inflection, as defined by the apices 48, 50, 52, 54 and the points of inflection 62, 64, and each cell 22 is non-symmetrical about the circumferential axis. In addition, as best shown in FIG. 2A, all the cells 22 in the same longitudinal row have the same orientation, and all the cells 22x in the same longitudinal row have the same orientation, but the cells 22 and 22x in the alternating rows are oriented in different directions.

Referring to FIG. 2B, when the stent 20 is in the compressed state, the internal points of inflection 64 are adjacent to each other. However, it is possible to position the compensating portions 60 along the third and fourth struts 36 and 42 so that the points of inflection 62, 64 can be nested within each other when the stent 20 is compressed. In such a case, when the stent 20 is compressed, an internal point of inflection 64 of the third strut 36 can be nested or fitted inside the space defined by an external point of inflection 62 of the fourth strut 42, and an internal point of inflection 64 of the fourth strut 42 can nested or fitted inside the space defined by an external point of inflection 62 of the third strut 36.

Figure 10:
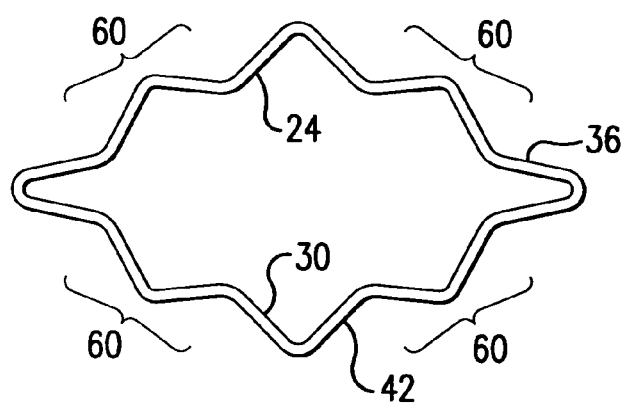
FIG. 10 is an enlarged side elevational view of a cell of portion of a stent according to another embodiment of the present invention.

As another example, it is possible to also provide the compensating portions 60 for the first and second struts 24 and 30, in addition to or in lieu of the compensating portions 60 for the third and fourth struts 36 and 42. For example, FIG. 10 illustrates a cell 22 where each strut 24, 30, 36 and 42 has a compensating portion 60.

Figure 3B:
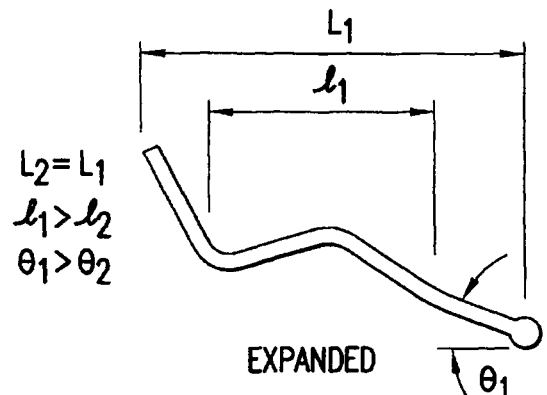
FIG. 3B illustrates the longitudinal component of a strut and its compensating portion of FIG. 3A when the stent is in its expanded state.
Figure 3C:
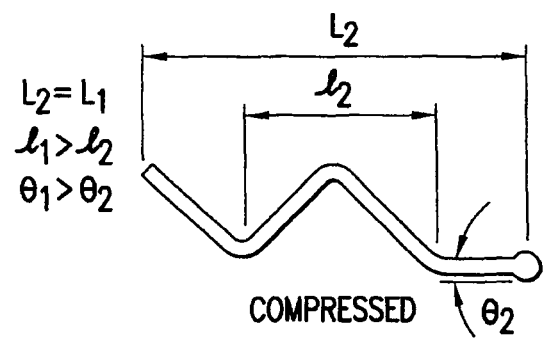
FIG. 3C illustrates the longitudinal component of a strut and its compensating portion of FIG. 3A when the stent is in its compressed state.

The compensating portions 60 function to compensate for the longitudinal foreshortening experienced by the struts 24, 30, 36, 42, thereby maintaining the stent 20 at substantially the same length at all times. This is accomplished by providing the compensating portions 60 with a natural bias and a springy nature, which together with its alternating segments, combine to shorten its length $l_1$ (see FIG. 3B) when compressed (i.e., $l_2$ in FIG. 3C is less than $l_1$). When allowed to expand, each compensating portion 60 is biased to return to its natural or original position, which increases its length from $l_2$ to $l_1$ to compensate for the foreshortening experienced by the longitudinal component of each strut 24, 30, 36, 42.

This effect is illustrated in FIGS. 2A, 2B, 3A, 3B and 3C. When the stent 20 is in its compressed state, the compensating portion 60 has an actual length which is less than its actual length when the compensating portion 60 is in its expanded state. When the compensating portion 60 is in the compressed state, its alternating segments have a higher amplitude and a smaller wavelength than when it is in the expanded state (compare FIGS. 3B and 3C). Thus, this difference between the actual lengths of the compensating portion 60 in its two compressed and expanded states compensates for the difference between $l_1$ and $l_2$ of the struts 36 and 42, so that the longitudinal lengths $L_1$ and $L_2$ of the strut (e.g., 36) are the same in both the compressed and expanded states. The lines 70 and 72 in FIGS. 2A and 2B also show that the relevant portion of the stent 20 does not experience any foreshortening.

Figure 4:
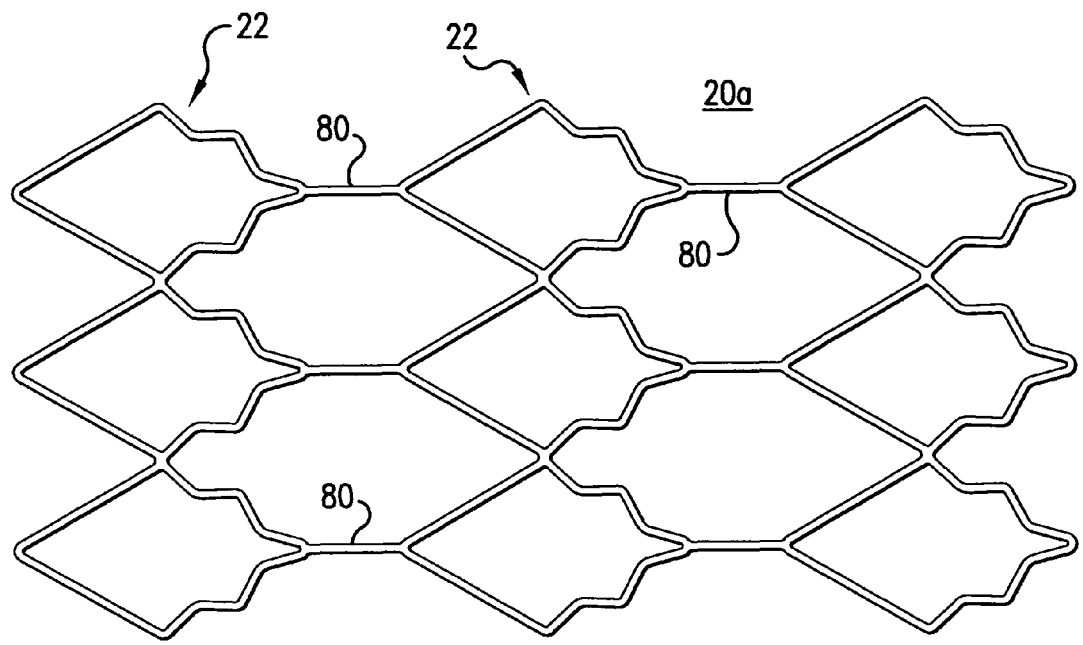
FIG. 4 illustrates a modification to the cell pattern of the stent of FIGS. 1 and 2A.

FIG. 4 illustrates a modification to the cell pattern for stent 20 shown in FIG. 2A. In particular, the cell pattern 20a in FIG. 4 provides a plurality of straight connecting members 80 that connect the first and second apices 48 and 50, respectively, of adjacent cells 22 in a longitudinal row R. These straight connecting members 80 can increase the flexibility of the stent, primarily in the longitudinal direction, but also to a small degree in the radial direction. In addition, one or more of these straight connecting members 80 can be omitted, either randomly or in a pattern (e.g., in a spiral pattern) to increase the flexibility of the stent at desired locations.

Figure 5:
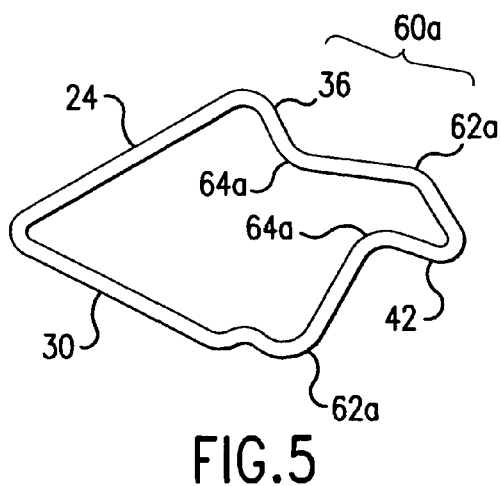
FIG. 5 is an enlarged side elevational view of a cell of portion of a stent according to another embodiment of the present invention.

Although the compensating portions 60 have been described in FIGS. 1-3 as assuming a particular configuration, it will be appreciated by those skilled in the art that the compensating portions 60 can assume other configurations without departing from the spirit and scope of the present invention. For example, the compensating portion 60 can be modified so that each has two points of inflection. This is illustrated in FIG. 5, where the third strut 36 has a compensating portion 60a that has one external point of inflection 62a and one internal point of inflection 64a, and the fourth strut 42 has a compensating portion 60a that has one external point of inflection 62a and one internal point of inflection 64a.

FIGS. 6-9 illustrate another type of compensating portion 90 according to the present invention which is configured to be a generally incomplete or C-shaped circle provided at one or more apices of the cells. For example, referring to FIG. 6A, each cell 22b is essentially the same as cell 22 in FIG. 3A, except that the compensating portions 60 have been replaced by compensating portions 90b that are provided at the location of the first and second apices 48 and 50 in such a manner that the first and second apices 48 and 50 are replaced by these compensating portions 90b. Each compensating portion 90b has a generally incomplete circular or C-shaped configuration, extending from the first end 26b, 32b, 38b or 44b of one of the struts 24b, 32b, 36b or 42b, respectively, then curling around in a circular fashion to the first end 26b, 32b, 38b or 44b of the adjacent strut 24b, 32b, 36b or 42b, respectively. The elements of the cell 22b that are the same as the elements of the cell 22 in FIG. 3A are provided with the same numeral designations except that a "b" has been added to the numeral designations in FIG. 6A.

Figure 6C:
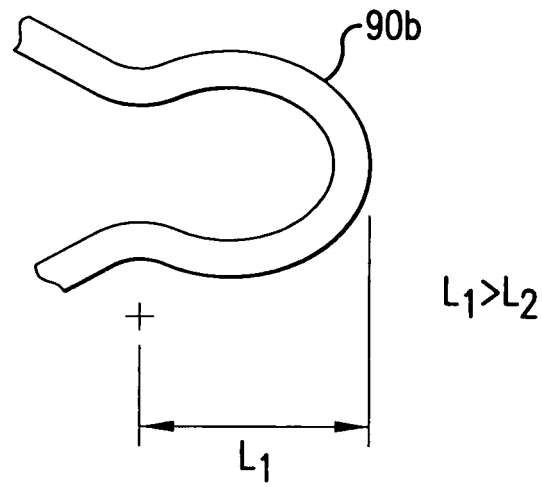
FIG. 6C illustrates the longitudinal component of a strut and its compensating portion of FIG. 6A when the stent is in its expanded state.
Figure 6D:
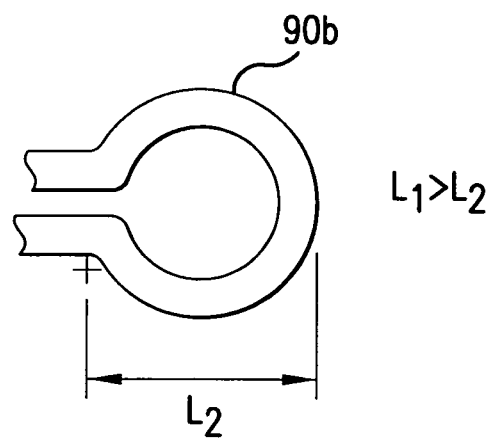
FIG. 6D illustrates the longitudinal component of a strut and its compensating portion of FIG. 6A when the stent is in its compressed state.

Each compensating portion 90b of each cell 22b is longitudinally (i.e., along a row) connected to a compensating portion 90b of an adjacent cell 22b by a straight connecting member 80b. The compensating portions 90b function in the same manner as the compensating portions 60 to compensate for the longitudinal foreshortening experienced by the struts 24b, 30b, 36b, 42b. In this regard, the generally circular curved configuration of the compensating portions 90b has one area of inflection 95 so that each compensating portion 90b has a shortened longitudinal length L2 when compressed, but has an increased longitudinal length L1 when allowed to expand so as to compensate for the foreshortening experienced by the longitudinal component of each strut 24b, 30b, 36b, 42b. This effect is illustrated in FIGS. 6B, 6C and 6D.

Figure 7:
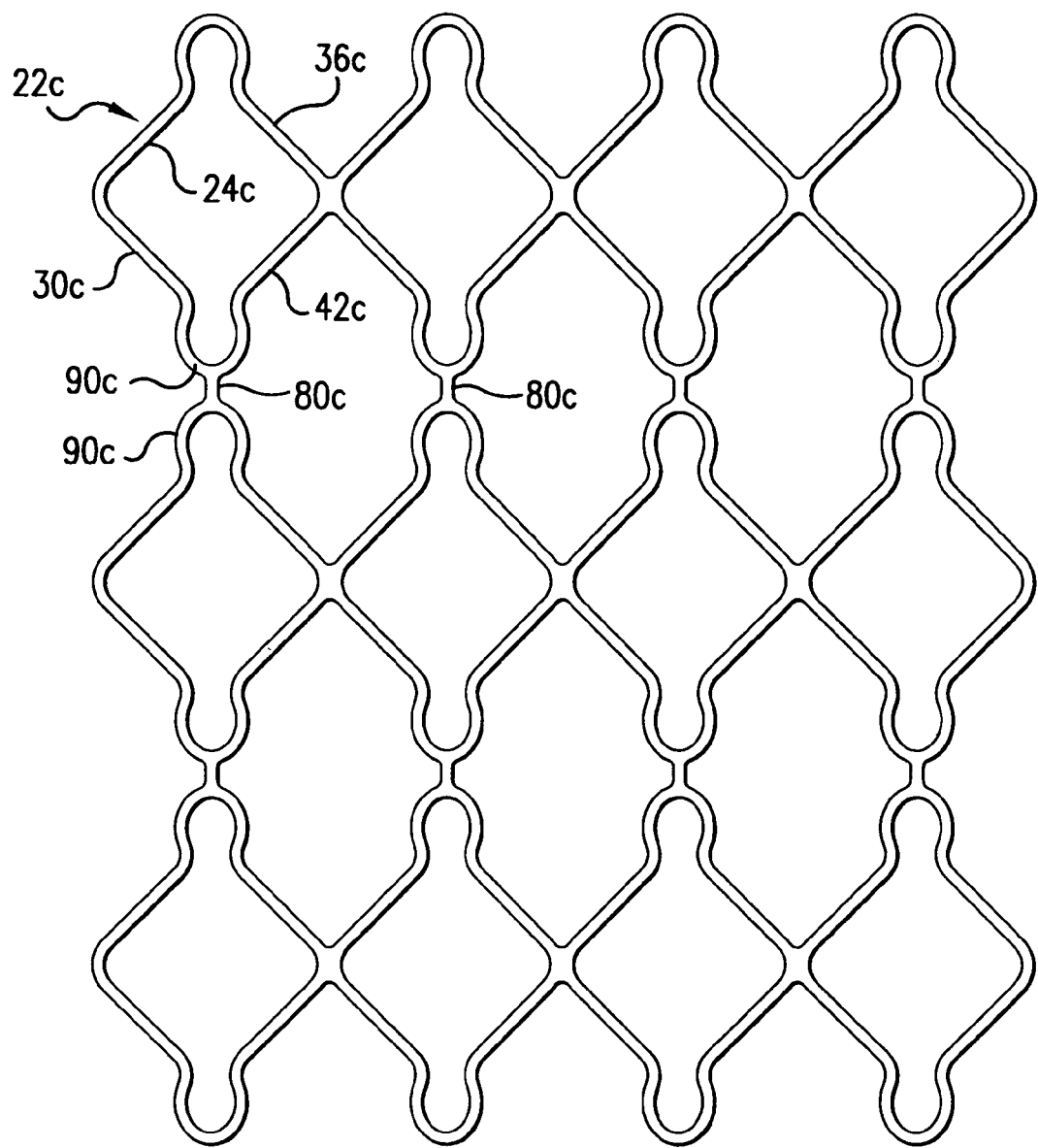
FIGS. 7-9 are side elevational views of portions of stents according to other embodiments of the present invention.

FIG. 7 illustrates a stent pattern in which each cell 22c is essentially the same as cell 22b in FIG. 6A, except that the compensating portions 90c are now provided at the third and fourth apices 52 and 54, respectively, in such a manner that the third and fourth apices 52 and 54 are replaced by these compensating portions 90c. Each compensating portion 90c has the same configuration as compensating portion 90b. The elements of the cell 22c that are the same as the elements' of the cell 22b in FIG. 6A are provided with the same numeral designations except that a "c" has been added to the numeral designations in FIG. 7. Each compensating portion 90c of each cell 22c can be transversely (i.e., along a column) connected to a compensating portion 90c of an adjacent cell 22c by a straight connecting member 80c.

Figure 8:
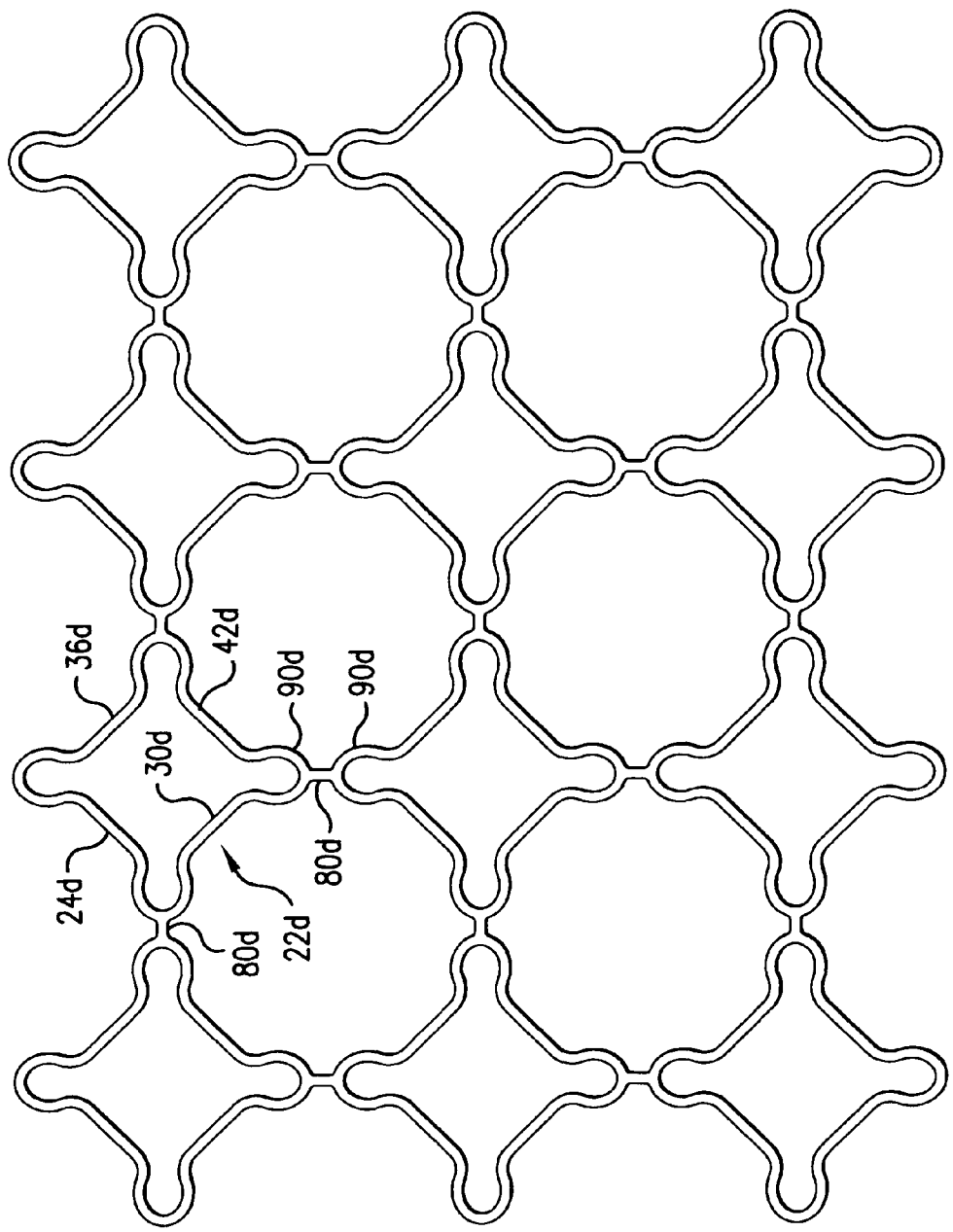

The principles illustrated in FIGS. 6A and 7 can be combined. For example, FIG. 8 illustrates a stent pattern in which each cell 22d has compensating portions 90d provided at all four apieces 48, 50, 52 and 54, in such a manner that each of the four apieces 48, 50, 52 and 54 is replaced by a compensating portion 90d. Each compensating portion 90d of each cell 22d can be either longitudinally or transversely connected to a compensating portion 90d of an adjacent cell 22d by a straight connecting member 80d. The elements of the cell 22d that are the same as the elements of the cells 22b and 22c are provided with the same numeral designations except that a "d" has been added to the numeral designations in FIG. 8.

Figure 9:
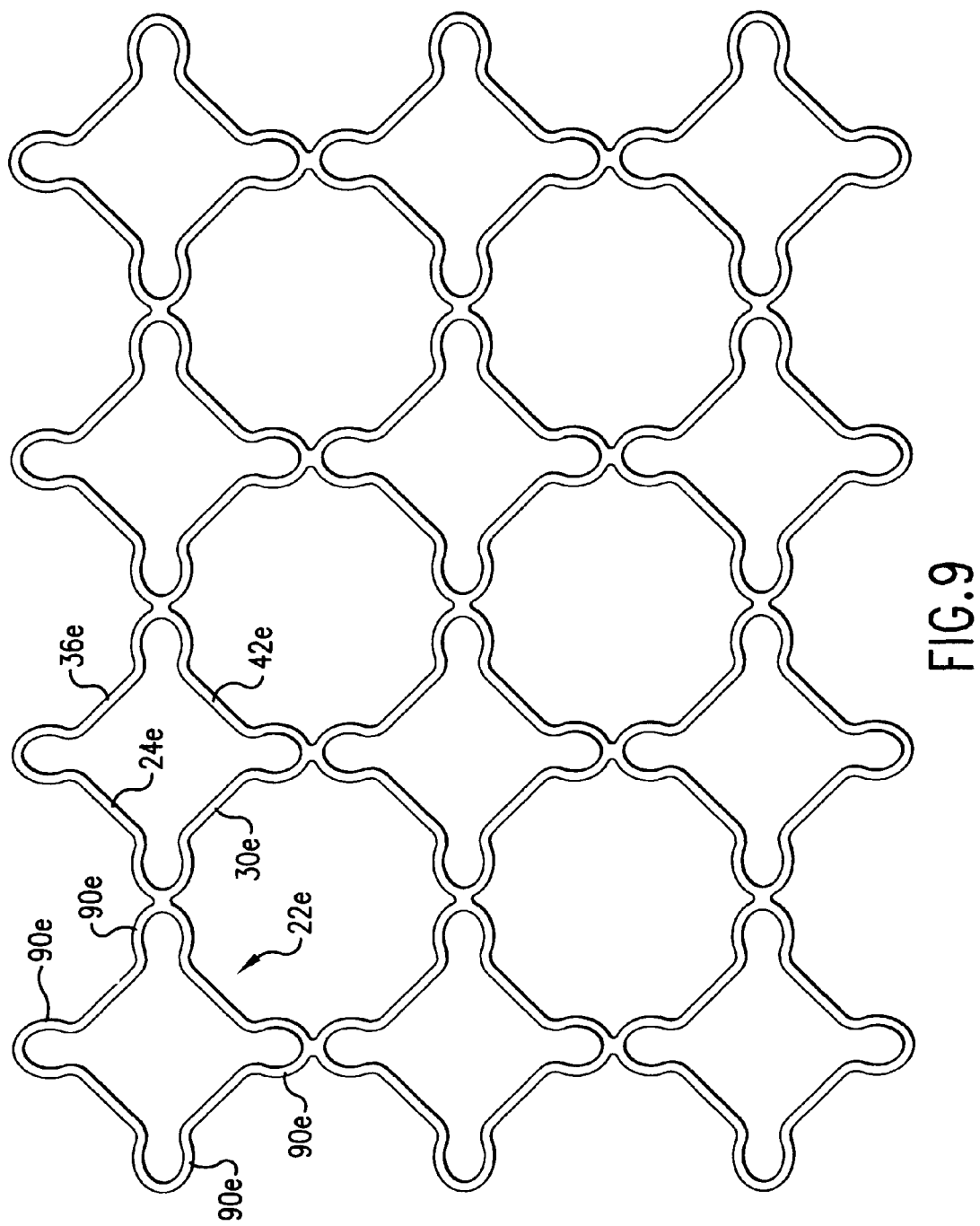

In addition, FIG. 9 illustrates a stent pattern which is the same as the stent pattern in FIG. 8, except that the connecting members 80d are omitted. Thus, each compensating portion 90e of each cell 22e in FIG. 9 is directly connected, either longitudinally or transversely, to a compensating portion 90e of an adjacent cell 22e. The elements of the cell 22e that are the same as the elements of the cell 22d are provided with the same numeral designations except that an "e" has been added to the numeral designations in FIG. 9.

Figure 11:
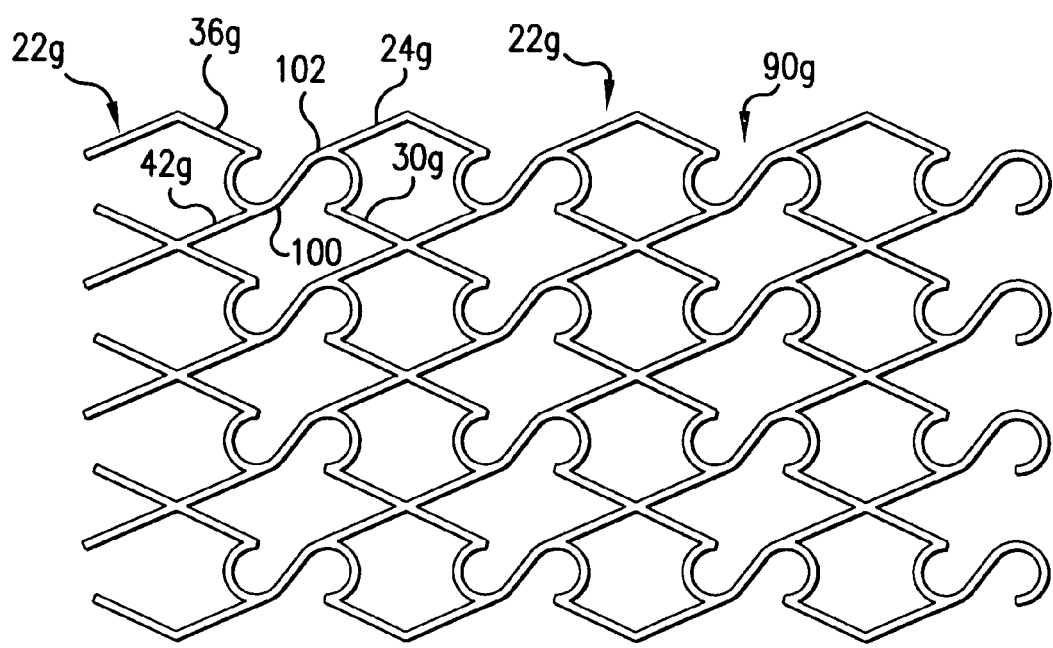
FIGS. 11-14 are side elevational views of portions of stents according to other embodiments of the present invention.
Figure 12:
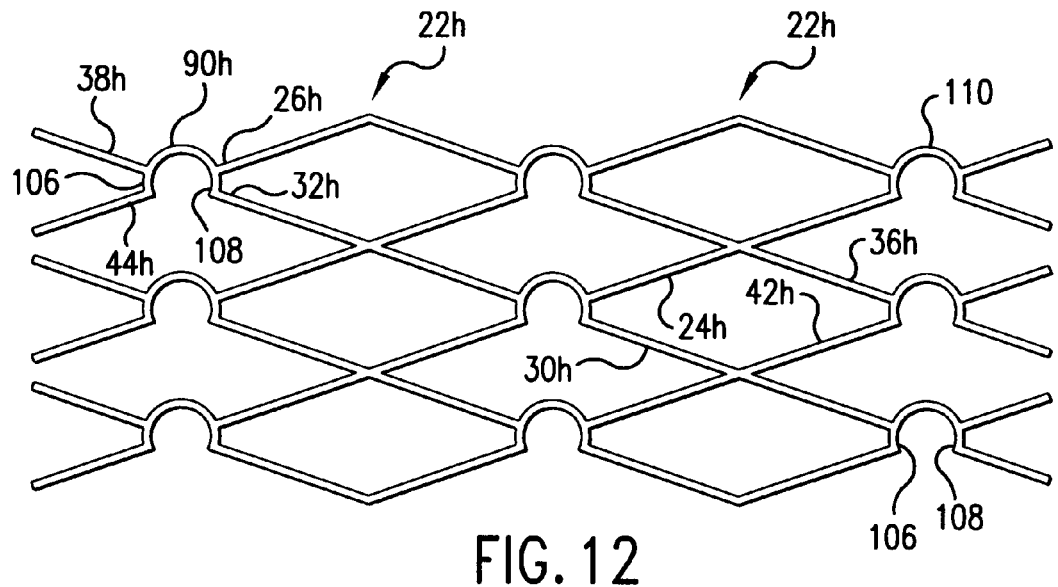

FIGS. 11 and 12 illustrate different types of compensating portions according to the present invention that embody the underlying principles described in connection with FIGS. 6-9. In FIG. 11, each cell 22g shares a compensating portion 90g with each longitudinally adjacent cell 22g. In particular, each compensating portion 90g is shaped like a sideway "S", with the top of the "S" coupled to a first cell 22g at the location of (and replacing) the first apex 48, and with the bottom of the "S" coupled to a longitudinally adjacent second cell 22g at the location of (and replacing) the second apex 50 of the second cell 22g. Thus, the sideway "S" shape of each compensating portion 90g defines two areas of inflection 100 and 102 that function to provide the compensation needed to avoid foreshortening according to the principles set forth in FIGS. 2-9 above. Otherwise, the elements of the cell 22g in FIG. 11 that are the same as the elements of the cell 22 in FIG. 3A are provided with the same numeral designations except that a "g" has been added to the numeral designations in FIG. 11.

Similarly, in FIG. 12, each cell 22h shares a compensating portion 90h with each longitudinally adjacent cell 22h. In particular, each compensating portion 90h is configured like the compensating portion 90b in FIG. 6, except that a first end 106 of the compensating portion 90h is connected to the first end 44h of the fourth strut 42h of a first cell 22h, with the compensating portion 90h curling around in a circular fashion to its second end 108, which is connected to the first end 32h of the second strut 30h of a longitudinally adjacent second cell 22h. The first end 38h of the third strut 36h of the first cell 22h is connected to the compensating portion 90h between the first and second ends 106 and 108 thereof, and the first end 26h of the first strut 24h of the second cell 22h is connected to the compensating portion 90h between the second end 108 and the first end 38h of the third strut 36h of the first cell 22h. Thus, the compensating portion 90h defines one area of inflection 110 between two longitudinally adjacent cells 22h that functions to provide the compensation needed to avoid foreshortening according to the principles set forth in FIGS. 2-9 above. Otherwise, the elements of the cell 22h in FIG. 12 that are the same as the elements of the cell 22 in FIG. 3A are provided with the same numeral designations except that an "h" has been added to the numeral designations in FIG. 12.

Figure 13:
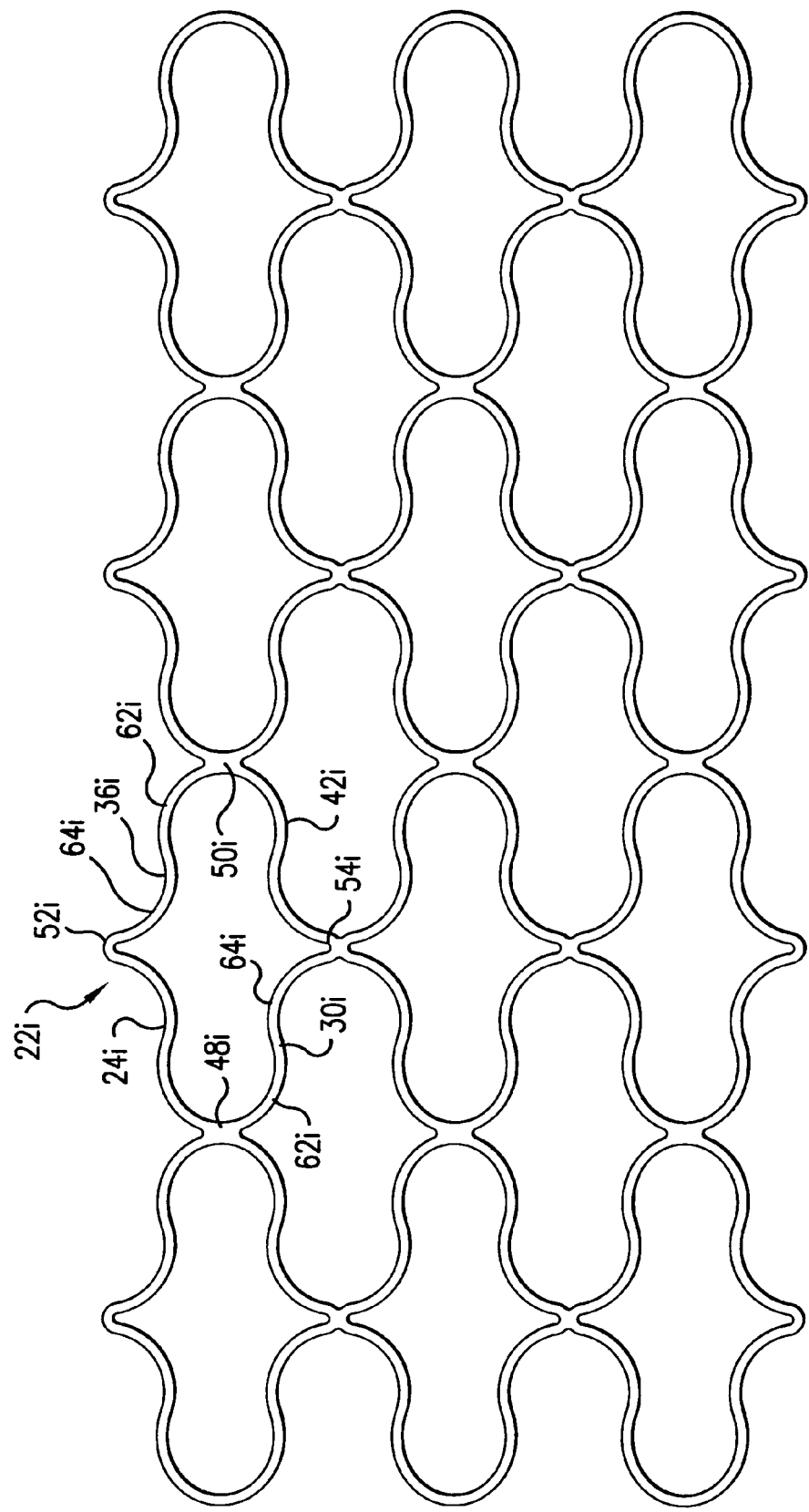

It is not necessary that the struts 24, 30, 36, 42 be straight. In this regard, the present invention provides cells having curved struts that provide at least one area of inflection to provide the compensation needed to avoid foreshortening according to the principles set forth in FIGS. 2-10 above. As a non-limiting example, FIG. 13 illustrates a stent pattern in which the cells 22i are essentially the same as the cell 22 in FIG. 3A, except that each strut 24i, 30i, 36i and 42i is now completely curved. Otherwise, the elements of the cell 22i in FIG. 13 that are the same as the elements of the cell 22 in FIG. 3A are provided with the same numeral designations except that an "i" has been added to the numeral designations in FIG. 13.

Figure 14:
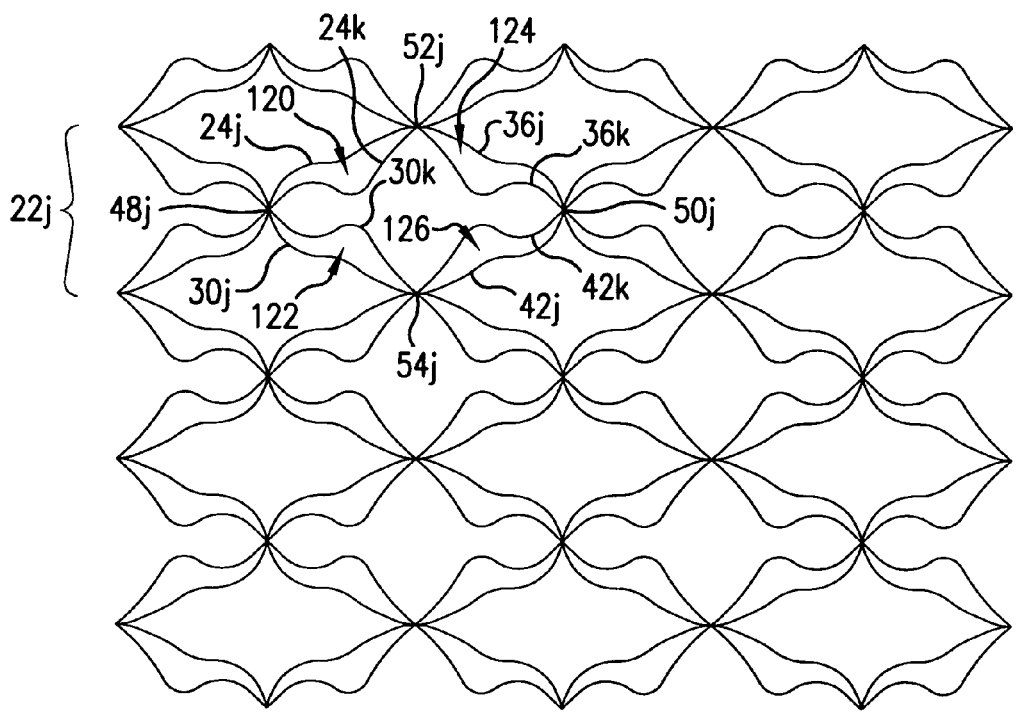

The cells 22j in the stent pattern in FIG. 14 borrow from the principles illustrated in FIGS. 3A and 13. Each strut in the cells 22j are made up of two strut pieces that have their respective ends connected at the apices 48j, 50j, 52j and 54j. In particular, the first strut 24j has an accompanying inner strut piece 24k whose ends are also connected to the apices 48j and 52j, the second strut 30j has an accompanying inner strut piece 30k whose ends are also connected to the apices 48j and 54j, the third strut 36j has an accompanying inner strut piece 36k whose ends are also connected to the apices 50j and 52j, and the fourth strut 42j has an accompanying inner strut piece 42k whose ends are also connected to the apices 50j and 54j. Each strut 24j, 30j, 36j, 42j and its accompanying inner strut piece 24k, 30k, 36k, 42k defines a smaller cell 120, 122, 124, 126, respectively. In this embodiment, the inner strut pieces 24k, 30k, 36k, 42k are shorter than each corresponding strut 24j, 30j, 36j, 42j.

Providing double struts to make up the desired cells 22j can provide certain benefits. First, the double-strut structure may increase the strength of the stent by providing radial and longitudinal resistance to compression and other changes in shape. Second, the resulting stent may have an increased expansion ratio. Third, the double-strut structure may reduce the tendency of the stent to recoil. Fourth, the resulting stent may have increased stent coverage and cells that have smaller sizes, thereby minimizing tissue in-growth. The double-strut embodiment of FIG. 14 can be especially useful in applications where the prosthesis requires increased support throughout the prosthesis while minimizing the potential for stent kink or breakage at certain regions along the stent.

Figure 15A:
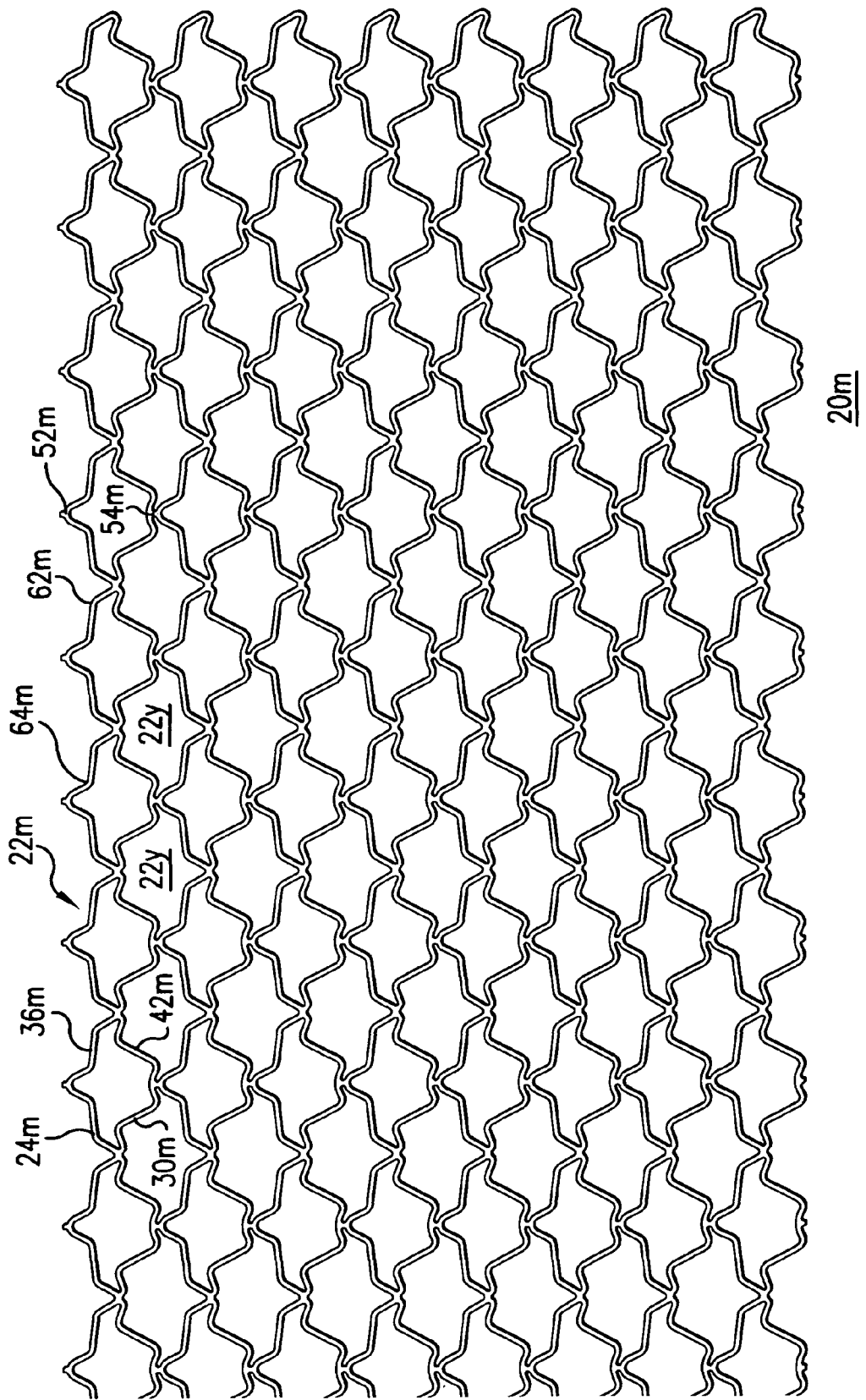
FIG. 15A is a side elevational view of a portions of a stent according to another embodiments of the present invention.
Figure 15B:
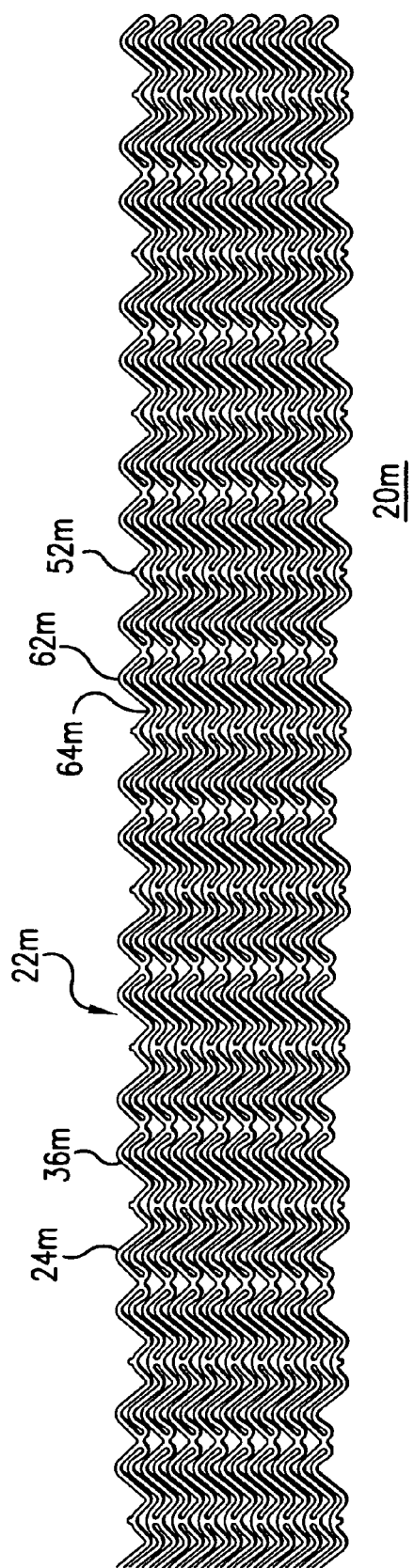
FIG. 15B is a side elevational view of the portion of FIG. 15A in its compressed state.

FIG. 15A illustrates a stent 20m in which the cells 22m are essentially the same as the cell 22i in FIG. 13, except that each strut 24m, 30m, 36m and 42m has less curvature. In fact, each strut 24m, 30m, 36m and 42m has one internal point of inflection 64m and one external point of inflection 62m. Otherwise, the elements of the cell 22m in FIG. 15 that are the same as the elements of the cell 22i in FIG. 13 are provided with the same numeral designations except that an "m" has been added to the numeral designations in FIG. 15. Similar to FIG. 2A, the pattern of cells 22m can define a second pattern of cells 22y that have about the same configuration as the cells 22m, but reversed about a horizontal axis defined by the apices 48m and 50m. Like the cells 22m, these second cells 22y are also arranged to form rows and columns of cells 22y. Each of the second cells 22y is defined by a separate strut from four separate cells 22m. FIG. 15B illustrates the stent 20m in the compressed state. One difference between the cell 22m and the other cells 22 herein is that the apex 54m in each cell 22m is inverted internally into the cell 22m, as opposed to extending externally from the cell 22m.

Figure 16:
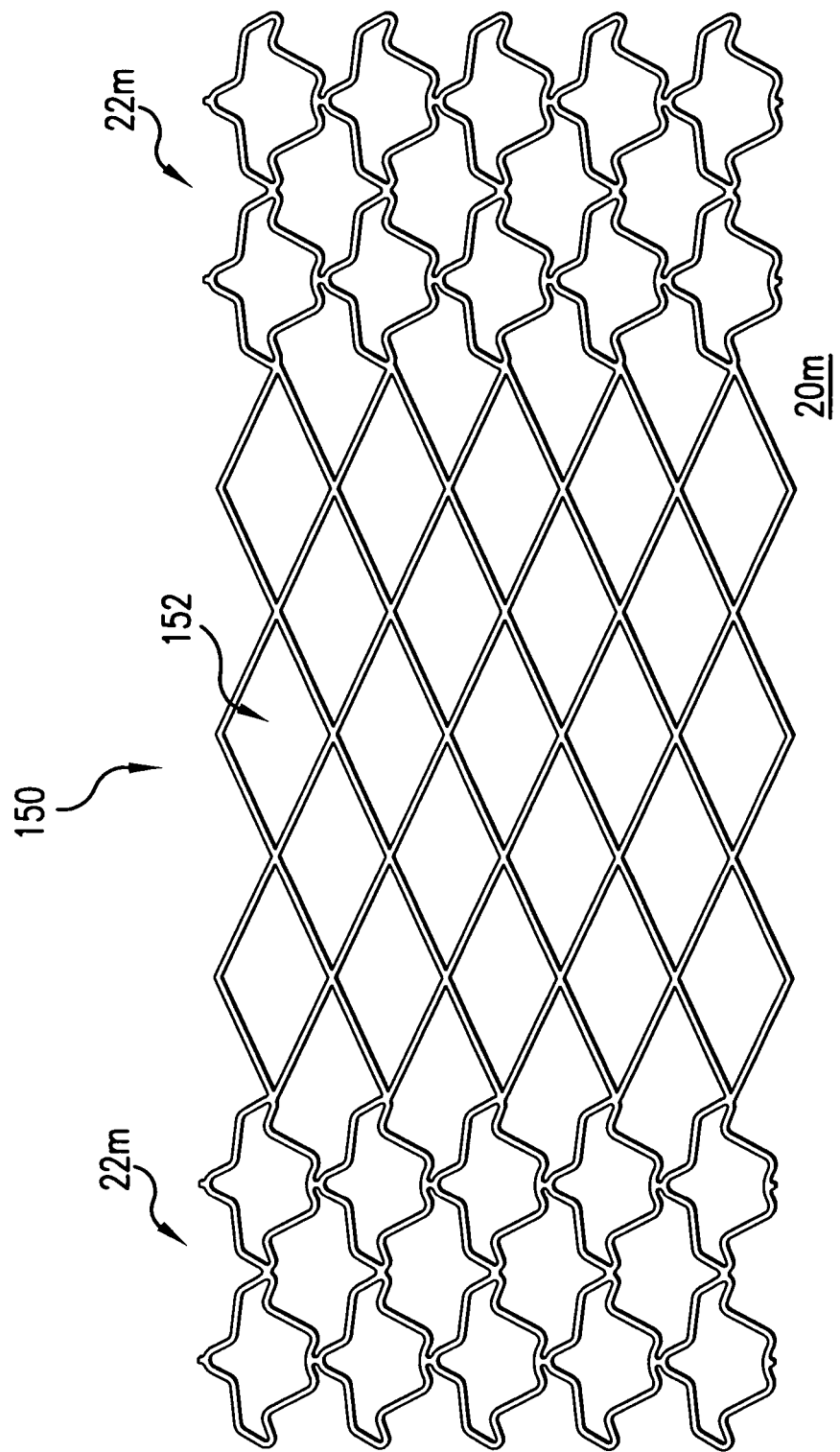

While the embodiments illustrated hereinabove illustrate stent patterns that are made up entirely of cells 22 that have compensating portions 60, it is also possible to intersperse cells that do not have any compensating portions 60. These principles will be illustrated in FIGS. 16-18 using the cell pattern 22m of FIG. 15. Referring first to FIG. 16, a stent 20m is illustrated as having a central portion 150 made up of a plurality of conventional zig-zag struts that do not have any compensating portions, and which form diamond-shaped cells 152. The two ends of the stent 20m is made up of the cell pattern 22m illustrated in FIG. 15. This configuration provides more rigidity in the central portion 150, and is better suited for use, for example, in the carotid arteries where more calcified lesions can be found at about the central portion 150, and where there is more potential for embolization in the central portion 150. This is because the diamond-shaped cells 152 are better suited to minimize embolization and prevent tissue in-growth.

Figure 17:
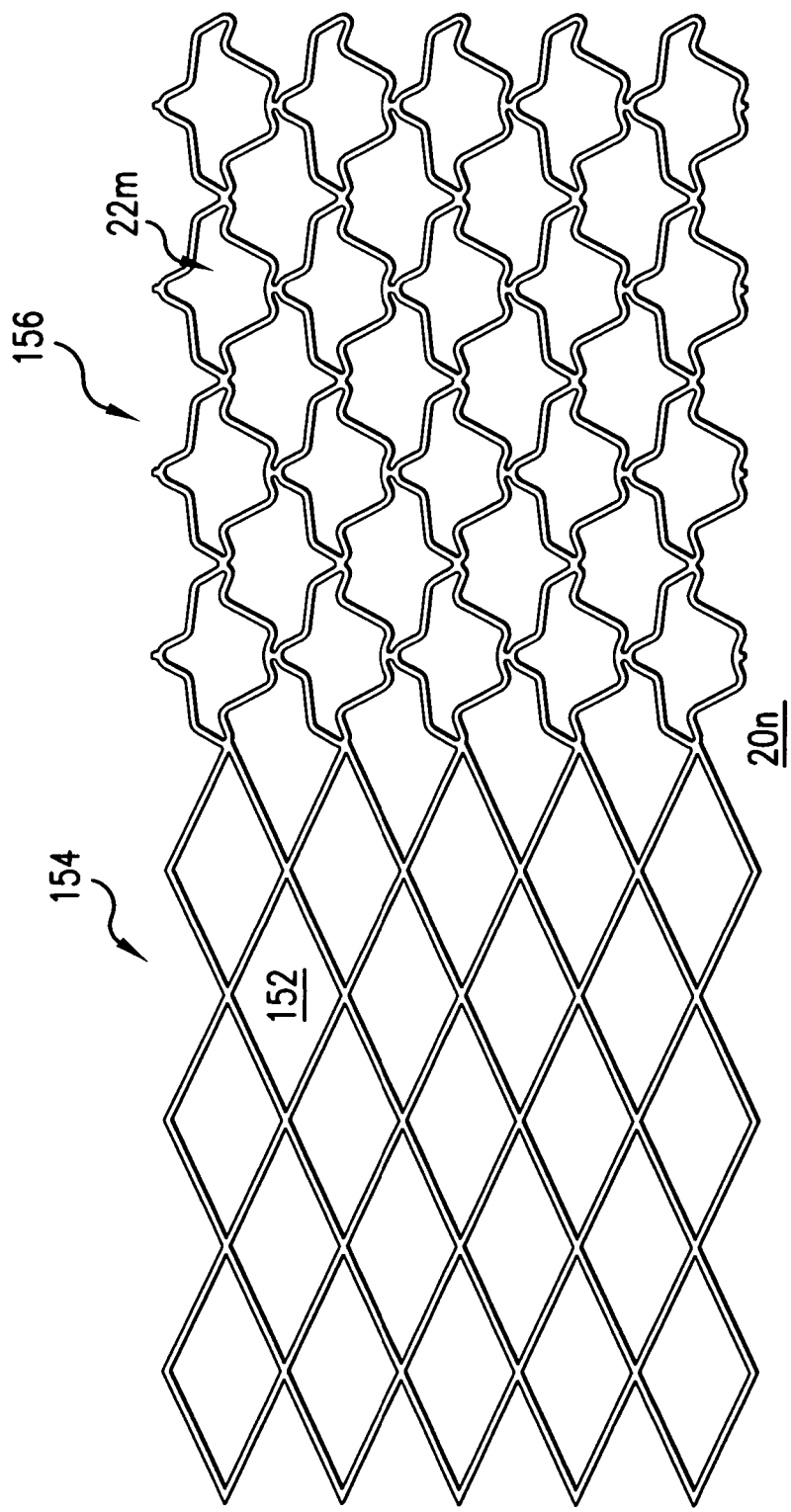

FIG. 17 illustrates a stent 20n having a first portion 154 made up of a plurality of conventional zig-zag struts that do not have any compensating portions, and which form diamond-shaped cells 152, and a second portion 156 that is made up of the cell pattern 22m illustrated in FIG. 15. The first portion 154 can be used to support a body vessel at a location that requires more rigidity, and the second portion 156 can be used to support a body vessel at a location that requires more flexibility. This configuration is better suited for use, for example, in the iliac arteries where the origin of the iliac arteries might have more calcified lesions where the first portion 154 would be intended to support.

FIG. 18 illustrates a stent 20p having rows 158 of cells 22m separated by one or more rows of the diamond-shaped cells 152. The rows 158 can be individual rows of cells 22m, or a plurality of rows of cells 22m. This configuration is useful in distributing the radial strength of the stent 20p while allowing for nonforeshortening and increased flexion at the desired locations (i.e., supported by the cells 22m). This configuration is best suited for use, for example, with curved vessels such as external iliac arteries.

A number of materials can be used to fabricate the stent 20 (including its struts 24, 30, 36, 42 and connecting members 80), depending on its method of deployment. These materials include, but are not limited to, Nitinol (which is a shape memory superelastic metal alloy whose use in stents is well-documented in the literature), stainless steel, tantalum, titanium, elgiloy, gold, platinum, or any other metal or alloy, or polymers or composites, having sufficient biocompatibility, rigidity, flexibility, radial strength, radiopacity and antithrombogenicity.

The stent 20 can be made from one of a number of methods, depending on the material of the stent 20 and the desired nature of deployment.

In a non-limiting first preferred method, the stent 20 is fabricated from a solid Nitinol tube with dimensions that are identical to the stent 20 when it is in the fully compressed state. The pattern of the stent 20 (i.e., its cells 22) is programmed into a computer-guided laser cutter which cuts out the segments between the struts and the connecting members (if any) in a manner which closely maintains the outside diameter and wall thickness of the stent 20.

After the cutting step, the stent 20 is progressively expanded until it reaches its fully expanded state. The expansion can be performed by an internal expansion fixture, although other expansion apparatus and methods can be used without departing from the spirit and scope of the present invention. The overall length of the stent 20 must be consistently maintained throughout the expansion of the stent 20 from its fully compressed to its fully expanded states.

Once the stent 20 has been expanded to its fully expanded state, it is heat-treated to "set" the shape memory of the Nitinol material so that it will fully return to its expanded dimensions at a temperature that is near body temperature. The stent 20 is then cleaned and electro-polished.

The next step is to compress the stent 20 again into a dimension which allows for delivery into a vessel, either through percutaneous delivery or through minimally invasive surgical procedures. Specifically, the stent 20 must be compressed into a smaller state so that it can be delivered by a delivery device to the desired location of the vessel. Any conventional delivery device could be used, such as but not limited to a tube, catheter, or sheath. This compression is accomplished by cooling the stent 20 to a low temperature, for example, zero degrees Celcius, and while maintaining this temperature, compressing the stent 20 to allow the stent 20 to be inserted inside the delivery device. Once inserted inside the delivery device, the stent 20 is held by the delivery device in the compressed state until it is released within the lumen of a vessel, at which time the stent will fully re-expand to its "set" dimensions as it equilibrates with body temperature.

In a non-limiting second preferred method, a balloon-expandable stent 20 can be fabricated by connecting a plurality of wires that have been bent or formed into the desired shapes for the struts 24, 30, 36, 42 and connecting members 80. The connection can be accomplished by welding, tying, bonding, or any other conventional method. Alternatively, wire electro-discharge machining or a computer guided laser cutter can be used. The wires are capable of experiencing plastic deformation when the stent 20 is compressed, and when the stent 20 is expanded. Upon plastic deformation of the stent 20 to either the compressed or the expanded state, the stent 20 remains in this state until another force is applied to plastically deform the stent 20 again.

While certain methods of manufacture have been described above, it will be appreciated by those skilled in the art that other methods of manufacture can be utilized without departing from the spirit and scope of the present invention.

The stent 20 can be deployed by a number of delivery systems and delivery methods. These delivery systems and methods will vary depending on whether the stent 20 is expanded by self-expansion, radial expansion forces, or radio frequency. These delivery methods are well-known in the art, and shall not be described in greater detail herein.

Thus, the present invention provides a stent having struts that include portions that compensate for the foreshortening effect. As a result, connecting members can be omitted from the stent designs according to the present invention, leading to at least the following benefits. First, cell sizes can be decreased so as to minimize "in-stent restenosis", and to provide better support to the vessel. Second, the stent can be provided with a more uniform structure that distributes any angulation or flexion of the stent more evenly along the full length of the stent, so that the stent can experience a more gradual curvature at bends rather than experiencing undesirable kinking at such regions. This further minimizes breakage or other damage to the stent. Of course, connecting members can be optionally added to increase the flexibility of the stent at certain desired areas.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A stent having a circumferential axis and comprising:
a plurality of closed cells disposed about the circumference of the stent, with each of the cells being non-symmetrical about the circumferential axis, the plurality of cells defining a first longitudinal row of cells and a second adjacent longitudinal row of cells, with each cell having a plurality of apices, and with cells in each longitudinal row having an apex directly connected to an apex of an adjacent cell in the same longitudinal row;
wherein each cell in the first and second longitudinal rows of cells has exactly ten points of inflection when the stent is expanded; wherein a point of inflection is defined by an apex
wherein all the cells in the first longitudinal row of cells have the same orientation and all the cells in the second longitudinal row of cells have the same orientation; and
wherein the cells in the first longitudinal row of cells are oriented in a different direction than the cells in the second longitudinal row of cells;
wherein the stent has a longitudinal axis, with each of the cells being symmetrical about the longitudinal axis;
wherein four of the ten points of inflection in each cell in the first longitudinal row of cells extend inside the cell; and
wherein six of the ten points of inflection in each cell in the first longitudinal row of cells extend outside the cell wherein the stent is adapted to be implanted in a lumen of a mammalian vessel.

2. The stent of claim 1, wherein each cell in the first longitudinal row of cells has a straight portion that is positioned between each of the points of inflection.

3. The stent of claim 1, wherein each cell in the second longitudinal row of cells has a straight portion that is positioned between each of the points of inflection.

* * * * *